United States Patent
Ash et al.

(10) Patent No.: US 8,631,352 B2
(45) Date of Patent: Jan. 14, 2014

(54) PROVIDER CARE CARDS

(75) Inventors: Michael Alan Ash, Parkville, MO (US); Thomas Anthony Fangman, De Soto, KS (US); Daniel Martin Feimster, Shawnee, KS (US); Theresa Marie Wavada, Lee's Summit, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 179 days.

(21) Appl. No.: 12/982,137

(22) Filed: Dec. 30, 2010

(65) Prior Publication Data

US 2012/0174014 A1 Jul. 5, 2012

(51) Int. Cl.
G06F 3/048 (2013.01)

(52) U.S. Cl.
USPC ............ 715/835; 715/764; 715/771; 715/803

(58) Field of Classification Search
USPC .................. 715/733, 751, 771–772; 705/2–3
See application file for complete search history.

(56) References Cited

U.S. PATENT DOCUMENTS

| | | | |
|---|---|---|---|
| 8,126,736 B2 | 2/2012 | Anderson et al. | |
| 2002/0038227 A1* | 3/2002 | Fey et al. | 705/3 |
| 2003/0023571 A1 | 1/2003 | Barnhill | |
| 2004/0199332 A1 | 10/2004 | Iliff | |
| 2005/0027562 A1 | 2/2005 | Brown | |
| 2006/0161457 A1 | 7/2006 | Rapaport et al. | |
| 2006/0205564 A1 | 9/2006 | Peterson | |
| 2008/0195422 A1* | 8/2008 | Nessinger et al. | 705/3 |
| 2008/0243548 A1* | 10/2008 | Cafer | 705/3 |
| 2008/0268413 A1* | 10/2008 | Leichner | 434/262 |
| 2008/0287746 A1 | 11/2008 | Reisman | |
| 2008/0288292 A1 | 11/2008 | Bi et al. | |
| 2009/0132284 A1 | 5/2009 | Fey et al. | |
| 2009/0164249 A1* | 6/2009 | Hunt et al. | 705/3 |
| 2009/0259493 A1 | 10/2009 | Venon et al. | |
| 2009/0319295 A1 | 12/2009 | Kass-Hout et al. | |
| 2010/0131883 A1* | 5/2010 | Linthicum et al. | 715/771 |
| 2010/0274576 A1* | 10/2010 | Young | 705/2 |
| 2010/0293003 A1 | 11/2010 | Abbo | |
| 2010/0299155 A1* | 11/2010 | Findlay et al. | 705/3 |
| 2011/0087501 A1* | 4/2011 | Severin | 705/3 |
| 2011/0093467 A1 | 4/2011 | Sharp et al. | |
| 2011/0201900 A1* | 8/2011 | Zhang et al. | 600/300 |
| 2012/0215784 A1 | 8/2012 | King et al. | |

OTHER PUBLICATIONS

Preinterview First Action Interview in U.S. Appl. No. 12/982,131 mailed Sep. 26, 2012, 42 pages.

(Continued)

*Primary Examiner* — Tuyetlien Tran
*Assistant Examiner* — Patrick Ramsey
(74) *Attorney, Agent, or Firm* — Shook Hardy & Bacon LLP (57) ABSTRACT

Methods, computer systems, and computer readable media for a provider care card graphical user interface are provided. The provider care card comprises a requirements display area configured to display at least one or more clinical measures relating to at least one patient, a measurements display area configured to display one or more measurements completed for one or more clinical measures relating to at least one patient, a first plurality of microdisplays configured to display a first visual indicator for each of the clinical measures that has been met, and a second plurality of microdisplays configured to display a second visual indicator for each of the clinical measures that has not been met.

13 Claims, 7 Drawing Sheets

(56) References Cited

OTHER PUBLICATIONS

First Action Interview Office Action in U.S. Appl. No. 12/982,131 mailed Nov. 7, 2012, 5 pages.

First Action Interview Office Action in U.S. Appl. No. 12/982,143 mailed Nov. 21, 2012, 7 pages.

Preinterview First Action Interview in U.S. Appl. No. 12/982,143 mailed Oct. 4, 2012, 10 pages.

Final Office Action in U.S. Appl. No. 12/982,131 mailed Apr. 24, 2013, 53 pages.

Final Office Action in U.S. Appl. No. 12/982,143 mailed May 1, 2013, 36 pages.

* cited by examiner

PROVIDER CARE CARDS

This application is related by subject matter to U.S. patent application Ser. No. 12/982,131, filed Dec. 30, 2010 and entitled "Patient Care Cards" and U.S. patent application Ser. No. 12/982,143, filed Dec. 30, 2010 and entitled "Health Information Transformation System" each of which is assigned or under obligation of assignment to the same entity as this application, and incorporated in this application by reference.

BACKGROUND

Traditionally, although a wealth of healthcare data exists with respect to a particular patient, the data is not in a form that easily utilized by computer applications. As well, the healthcare data is often dispersed throughout multiple sources, and it is difficult to assimilate and relate the same clinical concept from these multiple sources. Additionally, provider or patient graphical user interfaces that utilize this healthcare data are not user-friendly or, in the case of provider graphical user interfaces, do not present the provider with a comprehensive view of a patient's state of health.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Examples of the present invention are directed to methods, computer systems, and computer-readable media for use in transforming raw healthcare data from disparate sources into relevant healthcare data that may be utilized by a variety of healthcare applications. This transformation process occurs in a health information transformation system. As well, examples of the present invention are directed to graphical user interfaces in the form of provider care cards and patient care cards. Provider and patient care cards are built upon the relevant data generated by the health information transformation system. Provider care cards are user-friendly, intuitive graphical user interfaces that give providers a variety of tools they can use to more effectively care for their patients and improve the quality of healthcare they deliver. As well, patient care cards are also easy-to-use graphical user interfaces that help patients to partner with their providers and assume a more active role in managing their health. The ability to transform raw healthcare data into relevant healthcare data, which then may be used, for example, to facilitate patient care through the use of provider and patient care cards, is an important advantage in the never-ending quest to improve the quality of healthcare.

In one aspect of the invention, raw data is received from a plurality of data collectors, where the plurality of data collectors extract raw data from a plurality of raw data sources. In one aspect, the plurality of data collectors comprise electronic medical records crawlers, clinical and administrative data collectors, claims data collectors, document feed collectors and medical device feed collectors. In turn, the plurality of raw data sources may comprise electronic medical records, images, claims, data from patients or providers, documents, and medical devices. The raw data is sorted into unstructured raw data, structured data of non-standard nomenclature, and structured data of standard nomenclature. The sorted data is then transformed into relevant data through the use of natural language processing, nomenclature and ontology mapping, and distributed adaptive knowledge processing. The relevant data is loaded into a plurality of data repositories, and computer applications, including provider and patient care cards, are provided access to the plurality of data repositories. The plurality of data repositories may comprise real time transaction processing data repository, online analytical processing data repository, data mart data repository, search index data repository, and custom data repository.

In another aspect of the invention, a graphical user interface comprising a provider care card is provided. In one aspect, the provider care card comprises a requirements display area configured to display at least one or more clinical measures relating to at least one patient, and a measurements display area configured to display one or more measurements completed for one or more of the clinical measures. In addition, the invention comprises a first plurality of microdisplays configured to display a visual indicator for each of the clinical measures that has been met, and a second plurality of microdisplays configured to display a visual indicator for each of the clinical measures that has not been met. In another aspect, along with the features outlined above, the provider care card also comprises the first plurality of microdisplays and the second plurality of microdisplays arranged over a time period ranging from at least an initial point of provider/patient contact to at least a current point of provider/patient contact regardless of whether the clinical measure has been met or not met. In yet another aspect, along with the features outlined above, the first plurality of microdisplays are shaded a first color to indicate the clinical measure has been met, and the second plurality of microdisplays are shaded a second color to indicate the clinical measure has not been met.

In yet another aspect of the invention, a graphical user interface comprising a patient care card is provided. In one aspect, the patient care card comprises a requirements display area configured to display at least one or more clinical measures relating to a patient, and a visual indicator that changes depending on whether the clinical measure has been met. In another aspect, the patient care card comprises a requirements display area configured to display at least one or more clinical measures relating to a patient, and a measurements display area configured to display one or more measurements completed for one or more of the clinical measures relating to the patient. A trend display area is also provided that is configured to display at least one or more graphical representations of the clinical measures relating to the patient. As well, a visual indicator is provided that changes depending on whether the one or more clinical measures has been met. In yet another aspect of the invention, the patient care card comprises a patient input display area configured to receive inputs from the patient, where the inputs correspond to at least one or more of the clinical measures relating to the patient. The patient input display area is in addition to the requirements display area, measurements display area, trend display area and visual indicator as outlined above.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Examples of the present invention are directed to methods, computer systems, and computer-readable media for use in transforming raw healthcare data into relevant healthcare data that may be utilized by a variety of healthcare applications. The transformation process takes place in a health information transformation system. As well, examples of the present invention are directed to graphical user interfaces in the form of provider care cards and patient care cards. Provider and patient care cards are built upon the relevant data generated by the health information transformation system. Provider care cards are user-friendly, intuitive graphical user interfaces that allow providers to more effectively care for their patients. As well, patient care cards are also easy-to-use graphical user interfaces that help patients to partner with their providers and assume a more active role in managing their health. The ability to transform raw data into relevant healthcare data, which then may be used, for example, to facilitate patient care through the use of provider and patient care cards, is an important advantage in the never-ending quest to improve the quality of healthcare.

In one aspect of the invention, raw data is received from a plurality of data collectors, where the plurality of data collectors extract raw data from a plurality of raw data sources. In one aspect, the plurality of data collectors comprise electronic medical records crawlers, clinical and administrative data collectors, claims data collectors, document feed collectors and medical device feed collectors. In turn, the plurality of raw data sources may comprise electronic medical records, personal health records, images, documents, and medical devices. The raw data is sorted into unstructured raw data, structured data of non-standard nomenclature, and structured data of standard nomenclature. The raw data is then transformed into relevant data through the use of natural language processing, nomenclature and ontology mapping, and distributed adaptive knowledge processing. The relevant data is loaded into a plurality of data repositories, and computer applications, including provider and patient care cards, are provided access to the plurality of data repositories. The plurality of data repositories may comprise real time transaction processing data repository, online analytical processing data repository, data mart data repository, search index data repository, and custom data repository.

In another aspect of the invention, a graphical user interface comprising a provider care card is provided. In one aspect, the provider care card comprises a requirements display area configured to display at least one or more clinical measures relating to at least one patient, and a measurements display area configured to display one or more measurements completed for one or more of the clinical measures. In addition, the invention comprises a first plurality of microdisplays configured to display a visual indicator for each of the clinical measures that has been met, and a second plurality of microdisplays configured to display a visual indicator for each of the clinical measures that has not been met. In another aspect, along with the features outlined above, the provider care card also comprises the first plurality of microdisplays and the second plurality of microdisplays arranged over a time period ranging from at least an initial point of provider/patient contact to at least a current point of provider/patient contact regardless of whether the clinical measure has been met or not met. In yet another aspect, along with the features outlined above, the first plurality of microdisplays are shaded a first color to indicate the clinical measure has been met, and the second plurality of microdisplays are shaded a second color to indicate the clinical measure has not been met.

In yet another aspect of the invention, a graphical user interface comprising a patient care card is provided. In one aspect, the patient care card comprises a requirements display area configured to display at least one or more clinical measures relating to a patient, and a visual indicator that changes depending on whether the clinical measure has been met. In another aspect, the patient care card comprises a requirements display area configured to display at least one or more clinical measures relating to a patient, and a measurements display area configured to display one or more measurements completed for one or more of the clinical measures relating to the patient. A trend display area is also provided that is configured to display at least one or more graphical representations of the clinical measures relating to the patient. As well, a visual indicator is provided that changes depending on whether the one or more clinical measures has been met. In yet another aspect of the invention, the patient care card comprises a patient input display area configured to receive inputs from the patient, where the inputs correspond to at least one or more of the clinical measures relating to the patient. The patient input display area is in addition to the requirements display area, measurements display area, trend display area and visual indicator as outlined above.

Figure 1:
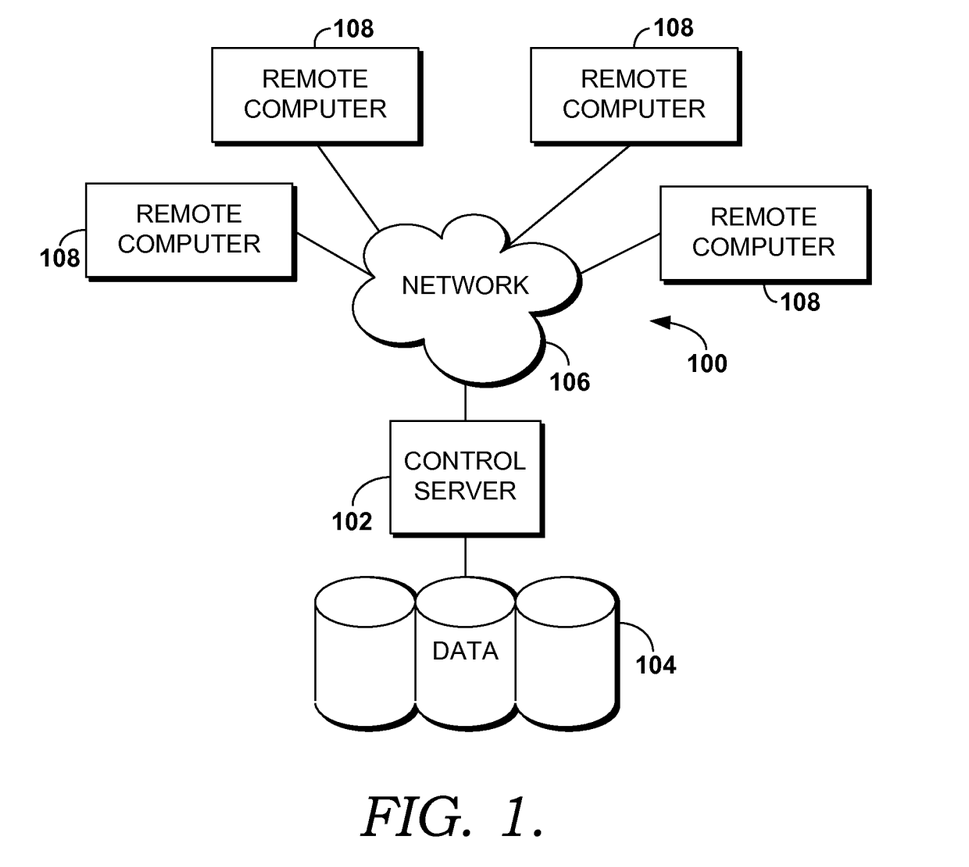
FIG. 1 is a block diagram of an exemplary computing environment suitable to implement embodiments of the present invention.

Having briefly described embodiments of the present invention, an exemplary operating environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. Computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other general purpose or special purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Combinations of any of the above also may be included within the scope of computer-readable media.

The computer storage media discussed above and illustrated in FIG. 1, including database cluster 104, provide storage of computer-readable instructions, data structures, program modules, and other data for the control server 102.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, those of ordinary skill in the art will appreciate that such components and their interconnection are well known. Accordingly, additional details concerning the internal construction of the control server 102 and the remote computers 108 are not further disclosed herein.

Health Information Transformation System

Figure 2:
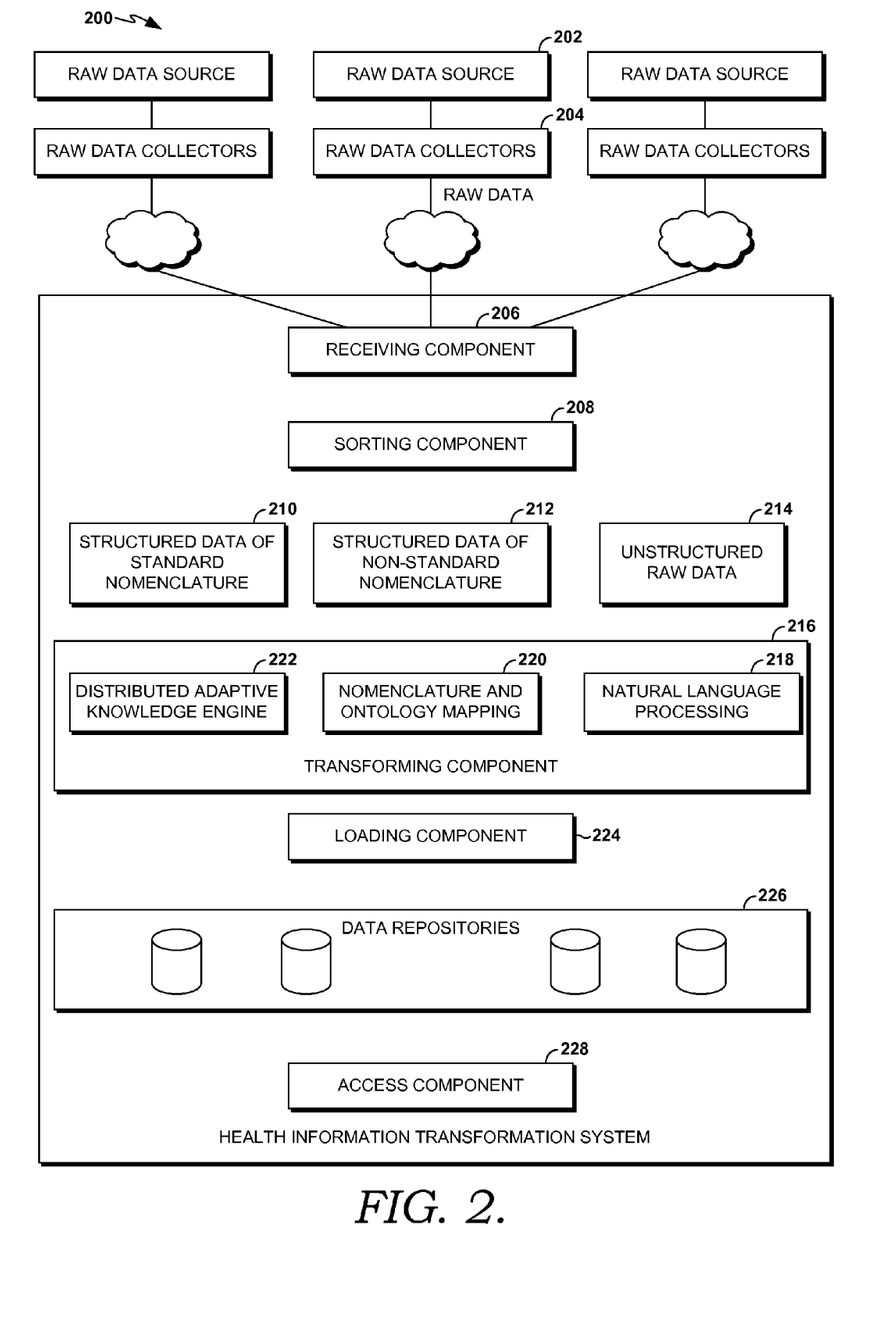
FIG. 2 depicts an exemplary framework of a health information transformation system suitable to implement embodiments of the present invention.

Turning now to FIG. 2, an exemplary framework of a health information transformation system 200 is provided. It will be understood by those of ordinary skill in the art that the arrangement shown in FIG. 2 is merely exemplary. While the health information transformation system is depicted as a single unit, one skilled in the art will appreciate that the health information transformation system is scalable. For example, the health information transformation system may in actuality include a plurality of computing devices in communication with one another. Moreover, the single unit depictions are meant for clarity, not to limit the scope of embodiments in any form.

A receiving component 206 is configured to receive raw data from a plurality of raw data collectors 204, where plurality of raw data collectors 204 is configured to collect raw data from a plurality of raw data sources 202. In one aspect of the invention, raw data sources 202 may comprise electronic medical record sources, images, documents, and medical devices. In turn, electronic medical record sources may comprise electronic clinical documents such as images, clinical notes, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. Images may comprise radiographic images, graphs, pictures, photographs, tables, and the like. Likewise, documents may comprise physician notes, physician reports, letters, and such. Finally, medical devices may comprise holter monitors, event monitors, post-event recorders, pre-symptom memory loop recorders, auto-detect recorders, implantable loop recorders, glucose monitoring devices, vital signs monitors, and such. Raw data sources 202 may be disparate in nature in that the raw data may be extracted from a variety of different sources as outlined above, and/or from different healthcare facilities and different providers.

Continuing, plurality of raw data collectors 204 may comprise electronic medical records crawlers, clinical and administrative data collectors, claims data collectors, document feed collectors, and medical device feed collectors. In one aspect of the invention, raw data collector 204 collects Health Level Seven (HL7) or Continuity of Care Document (CCD) data. HL7 and CCD develop standards for the electronic exchange of healthcare information and is involved in the sharing of this information. In another aspect of the invention, raw data collector 204 collects Electronic Data Interchange (EDI) data. In one aspect, EDI involves the electronic exchange of standardized information pertaining to insurance claims. EDI data includes uniform data extracted from claims originating from different insurance companies. As well, raw data collector 204 may obtain or collect raw data through e-mail, facsimile, retrieval from the document source, as well as from the medical devices discussed above.

After the raw data is received by receiving component 206, it is sorted by a sorting component 208 into structured data of standard nomenclature 210, structured data of non-standard nomenclature 212, and unstructured raw data 214. Structured data of standard nomenclature 210 may comprise data that is in a computer-useable format suitable for use by a distributed adaptive knowledge engine component 222. For example, data is structured if it is coded with the proper International Classification of Diseases, 9$^{th}$ Revision, Clinical Modification (ICD-9-CM) code. In turn, the data has standard nomenclature if it is in a computer-useable language such as Systemized Nomenclature of Medicine (SNOMED) or Logical Observation Identifiers Names and Codes (LOINC). By way of illustrative example, and not by limitation, structured data of standard nomenclature 210 may comprise clinical and administrative data that conforms to the standards set forth by HL7 or other standard-setting bodies, as well as insurance claims information retrieved from EDI.

Continuing, structured data of non-standard nomenclature 212 may comprise data that needs additional processing before it is suitable for processing by distributed adaptive knowledge engine component 222. For example, the data might have the proper ICD-9-CM code but not be in a standard nomenclature, such as, for example, SNOMED or LOINC. Structured data of non-standard nomenclature 212 may comprise patient information obtained from an electronic medical records source. By way of illustrative example, a piece of patient-specific raw data extracted from an electronic medical record source may be the term "pityriasis." The term "pityriasis" has the proper ICD-9-CM code of, for example, 696.3, but it is not in standard SNOMED nomenclature. The term "pityriasis" is given standard SNOMED nomenclature (i.e. 77252004). Now the term "pityriasis" can be processed by distributed adaptive knowledge engine component 222. Additionally, unstructured raw data 214 may comprise data obtained from a provider's typed reports, notes, documents and letters. This data is not structured correctly and is not in standard nomenclature. Unstructured raw data 214 needs to be converted from human speech or documentation to a computer-useable language.

A transforming component 216 transforms the sorted data into relevant data through the use of a natural language processing component 218, a nomenclature and ontology mapping component 220, and distributed adaptive knowledge engine component 222. In one embodiment, natural language processing component 218 transforms unstructured raw data 214 into structured data of non-standard nomenclature 212 or structured data of standard nomenclature 210.

As mentioned above, unstructured raw data is converted from human speech or input into a computer-useable language using natural language processing component 218. An exemplary natural language processing system may include Discern nCode™ by Cerner. By way of illustrative example, natural language processing component 218 scans a physician's dictated note and identifies clinical concepts with codified meanings. For example, a physician's note pertains to a patient who has previously been diagnosed with diabetes and is now suffering from diabetic retinopathy. Natural language processing component 218 identifies the clinical concept "diabetic" and the clinical concept "retinopathy." Both of these terms have an established codified (i.e. ICD-9-CM code) meaning. Next, natural language processing component 218 labels the identified clinical concepts as positive, suspected, or negative based on the analysis, understanding, and context of the text within the note. In this case, the clinical concepts "diabetic" and "retinopathy" would both be labeled positive. Natural language processing component 218 then translates the clinical concept into a health concept. Using the example given above, the clinical concept "diabetic" plus "retinopathy" is translated into a health concept "diabetic retinopathy" by applying the correct ICD-9-CM codes and the standard SNOMED nomenclature. The health concept "diabetic retinopathy" is now considered structured data of standard nomenclature 212.

In another aspect, unstructured raw data 214 may be transformed into structured data of non-standard nomenclature. As mentioned above, the unstructured data is transformed into structured data by codifying the data. But the raw data may be given non-standard nomenclature, such as, for example Multum®, instead of standard nomenclature. The non-standard nomenclature may be used if the standard nomenclature is not complete, or does not have the level of detail required with respect to a specific piece of raw data. As well, only non-standard nomenclatures that are already mapped into the system will be utilized.

Nomenclature and ontology mapping component 220 is configured to transform structured data of non-standard nomenclature 212 into structured data of standard nomenclature 210. By way of illustrative example, nomenclature and ontology mapping component 220 receives structured data of non-standard nomenclature 212 comprising a discrete health concept such as "skin eruption" or "rash exanthem" and associates that discrete health concept with a broader health concept such as "eruption of skin." In turn, the broader health concept, "eruption of skin," may be associated with a still broader health concept "rash," where "rash" is structured data of standard nomenclature 210 suitable for processing by distributed adaptive knowledge engine component 222. Still further, nomenclature and ontology mapping component 220 may receive structured data of non-standard nomenclature 212 in the form of related discrete health concepts such as "skin eruption," "comedone," "weal," and "pityriasis" and associate the related discrete health concepts with the broader health concept "eruption of skin." In turn, based on existing relationships within nomenclature and ontology mapping component 220, the broader health concept "eruption of skin" is associated with the health concept "rash", where "rash" is structured data of standard nomenclature 210.

Distributed adaptive knowledge engine component 22 is configured to transform structured data of standard nomenclature 210 into relevant data. In one aspect of the invention, distributed adaptive knowledge engine component 222 may be an artificial intelligence (AI) engine configured to provide decision support concerning which structured data of standard nomenclature 210 should be selected and sent on in the form of relevant data to a loading component 224 for eventual loading into a plurality of data repositories 226. In general terms, distributed adaptive knowledge engine component 222 utilizes multi-agents that collaborate with each other and interface with external systems, services and users and has the ability to monitor changes and incorporate past knowledge into decision making in order to generate and evaluate alternative plans or adapt plans to handle conflict resolution and critical constraints. A multi-agent virtual operating system provides efficient means to build complex systems composed of autonomous agents with the ability to be reactive, persistent, autonomous, adaptable, mobile, goal-oriented, context aware, cooperative and able to communicate with other agents and non-agents. Intelligence is achieved within agents by way of support provided by a rich ontology within a semantic network. For example, a multi-level of collaborating agents allows low level agents to transform data so that it can be passed on to another agent, and to continue the data transformation until the data has been completely transformed from bits of data which may sometimes represent incomplete, outdated, or uncertain data, to a form a usable collection of data with rich meaning. In this example, when it becomes necessary to attack complex problems the agent is permitted to constrain and narrow its focus at an individual level to support decomposition. Domain specific agents can be leveraged in some embodiments to use an ontology to manage local domain specific resources.

Distributed adaptive knowledge engine component 222 handles process management, scheduling, memory, resource management, Input/Output ("I/O"), security, planning, as well as other processes traditionally handled by operating systems, and in some embodiments includes memory, which may include short, intermediate, and/or long term memory, I/O, internal agent blackboard, context switching, kernel, swapper, device resource management, system services, pager, process managers, and logging, auditing, and debugging processes. In some embodiments, distributed adaptive knowledge engine component 222 is a distributed virtual operating system. Distributed adaptive knowledge engine component 222 may also include a Symantec Engine, which provides the platform for complex agents and primitive agents. On top of the agents layers are applications, such as agent solver. Agent solvers may include a finite state machine instantiated and executed to determine a patient's conditions and recommended treatments. Other agent solvers may include searching, including heuristic and traditional searching; list; constraint satisfaction; heuristic informed; hill climbing; decision tree; simulated annealing; graph search; A* search; genetic algorithm; evolutionary algorithm; tabu search; logical inference; fuzzy logic; forward and backward chaining rules; multi-criteria decision making; procedural; inductive inference; pattern recognition; neural fuzzy network; speech recognition; natural language processing; decomposition; divide and conquer; goal tree and sub-goal tree; state machine; function decomposition; pattern decomposition; and other decision processing applications.

As well, distributed adaptive knowledge engine component 222 may perform some interpretation on structured data of standard nomenclature 210, where the interpretation takes place outside the context of a specific patient. By way of illustrative example, and not by limitation, distributed adaptive knowledge engine component 222 may identify structured data of standard nomenclature 210 corresponding to a creatinine value of 2.0 milligrams per deciliter (creatinine is a measure of kidney function), where normal levels of creatinine range from 0.5 milligrams per deciliter to 1.2 milligrams per deciliter. Without looking at the creatinine value in the context of a specific patient, distributed adaptive knowledge engine component 222 determines that the creatinine is elevated and, based on this determination, selects and transforms this piece of structured data of standard nomenclature 210 into relevant data.

Loading component 224 is configured to load the relevant data into a plurality of data repositories 226. In one aspect of the invention, plurality of data repositories 226 may be optimized for specific use cases. By way of illustrative example, at least one data repository of plurality of data repositories 226 may be optimized to store relevant data pertaining to Patient X or Provider Y. The relevant data would comprise all of the relevant data specifically relating to Patient X or Provider Y. A data repository that is optimized for this kind of use is said to be identified and may be suitable for providing in-depth information on Patient X or Provider Y. On the other hand, another data repository of plurality of data repositories 226 may be optimized to store a small subset of relevant data corresponding to a plurality of different patients or providers. A data repository optimized for this kind of use is said to be de-identified and may be suitable, for example, for providing a specific piece of health information on all patients residing within a certain zip code area.

In another aspect of the invention, plurality of data repositories 226 may comprise a master patient index, where a master patient index references all patients known to an area, healthcare facility, organization, enterprise, and the like. In yet another aspect of the invention, plurality of data repositories 226 may comprise at least one of real-time transaction processing data repository, online analytical processing data repository, search index data repository, data mart data repository, and custom data repository. Real-time transaction processing data repository stores relevant data used in real-time transaction processing. These transactions are processed as they occur and are not part of a group of transactions. Further, online analytical processing data repository stores relevant data that can be used to compare relationships between different sets of data. Search index data repository may be used to quickly and accurately locate relevant documents in response to a search query, while data mart data repository stores relevant data used to create decision support. Finally, custom data repository may be customized according to the preferences of a user.

In one aspect of the invention, online analytical processing data repository may be either identified or de-identified. As outlined above, online analytical processing data repository may be identified if it stores relevant data that relates to a specific patient or provider. Alternatively, online analytical processing data repository may be de-identified if it stores relevant data relating to a plurality of patients. In another aspect of system 200, data mart data repository may also be identified or de-identified. In one aspect, relevant data stored in an identified data mart data repository may be used to create decision support for a patient as outlined further below.

An access component 228 is configured to provide access to plurality of data repositories 226. In one aspect of the invention, access component 228 may provide access to healthcare applications and services comprising at least one of eVisit, care card, condition management, evaluation and management (E/M) coding, quality reporting, and search applications. Still further, in another aspect, access component 228 may provide a provider care card application and a patient care card application access to data mart data repository. These two applications use the relevant data stored in data mart data repository to create graphical user interfaces in the form of provider care cards and patient care cards. Provider care cards have a number of different capabilities that assist providers in caring for their patients, while patient care cards are designed to help patients assume a more active role in managing their health.

As mentioned above, relevant data stored in data mart data repository may be used to create decision support for a patient. The provider/patient care card application, in one example, may utilize a typical rules engine to create decision support for the care card application. The rules engine may determine actions or dispositions with respect to a patient by applying a set of pre-defined rules to a pre-determined number of conditions or treatments. In another aspect, the provider/patient care card application may utilize an artificial intelligence (AI) engine, such as, for example, distributed adaptive knowledge engine component 222, that uses relevant data stored in an identified data mart data repository to provide flexible, adaptive, decision support for a patient. For example, the AI engine in the care card application may use the relevant data along with a set of parameters that specify information about drugs, contra-indications, diagnoses, conditions, and the like to instantiate and apply a program to determine recommended treatments for a patient. This process takes place in the context of a specific patient unlike both the rules engine mentioned above. By way of illustrative example, and not by limitation, the AI engine in the care card application identifies relevant data stored in data mart data repository corresponding to a creatinine level of 2.0 milligrams per deciliter for Patient X. A typical rules engine would automatically generate an alert to a provider based on the elevated level. But distributed adaptive knowledge engine component looks at the creatinine level in the context of Patient X. Patient X, for example, has end-stage renal disease and will always have an elevated creatinine level. Distributed adaptive knowledge engine component processes all of the relevant data relating to Patient X and determines that while the creatinine level is elevated in general, an alert does not need to be provided because the creatinine level is within normal range for Patient X.

Figure 3:
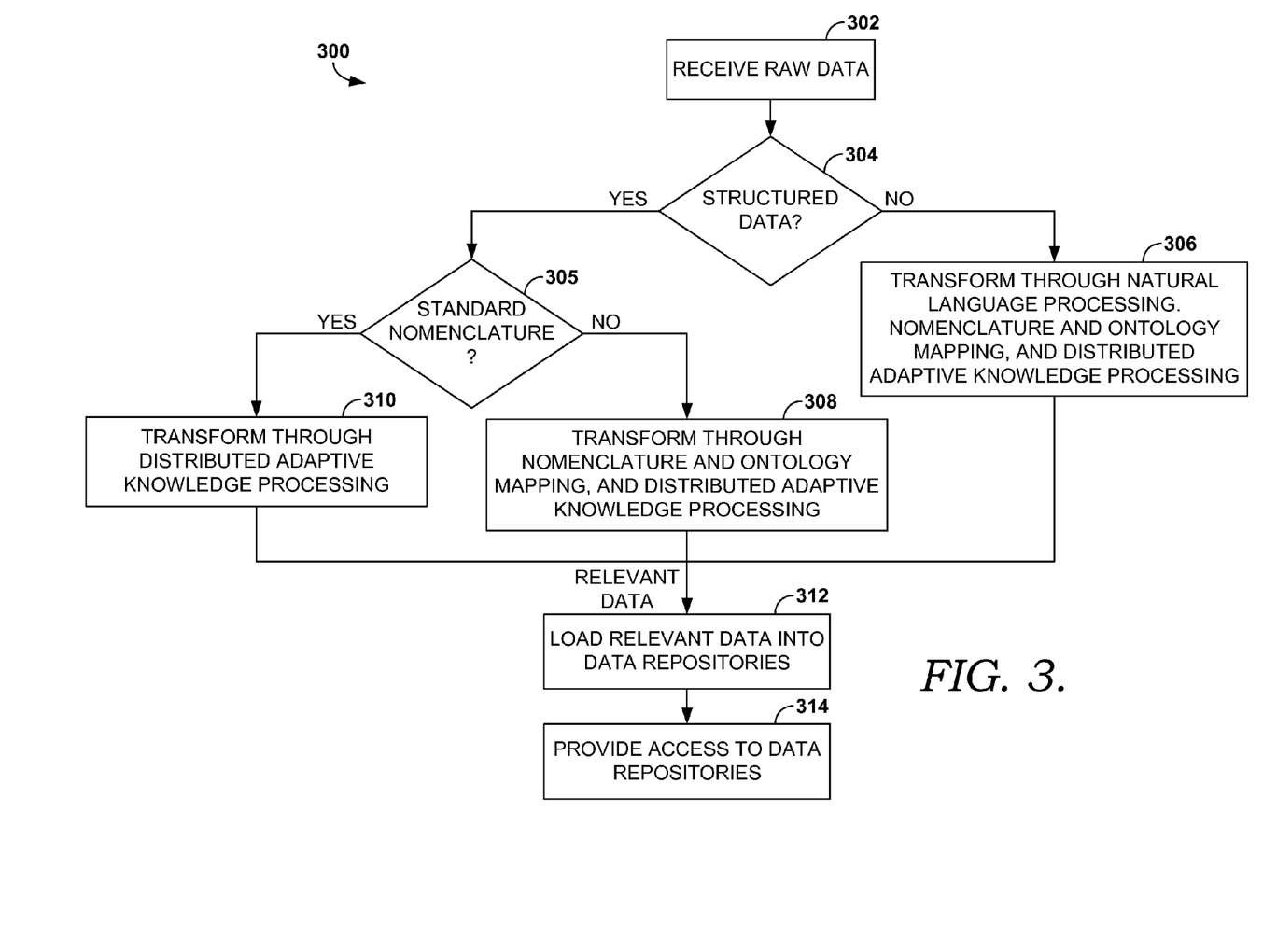
FIG. 3 depicts a flow diagram of a method to transform health information in accordance with an embodiment of the present invention.

Turning now to FIG. 3, a flow diagram of a method 300 to transform raw healthcare data into relevant healthcare data is provided. The information outlined above with respect to FIG. 2 is also applicable to method 300. At step 302, raw data is received from a plurality of data collectors, where the plurality of data collectors extract raw data from a plurality of data sources. At step 304 the raw data is sorted by making a determination as to whether the raw data is structured. If the raw data is structured, a determination is made at step 305 as to whether the structured data has standard nomenclature or non-standard nomenclature. If the raw data is structured and has standard nomenclature it is transformed at step 310 into relevant data through distributed adaptive knowledge processing. If it is determined at step 305 that the raw data is structured but does not have standard nomenclature, it is transformed at step 308 into relevant data through nomenclature and ontology mapping, and distributed adaptive knowledge processing. Returning to step 304, if it is determined that the raw data is not structured data, the raw data is transformed into relevant data at step 306 through natural language processing, nomenclature and ontology mapping, and distributed adaptive knowledge processing. At step 312, the relevant data is loaded into a plurality of data repositories, and at step 314 access to the plurality of data repositories is provided.

Provider Care Cards

Figure 4:
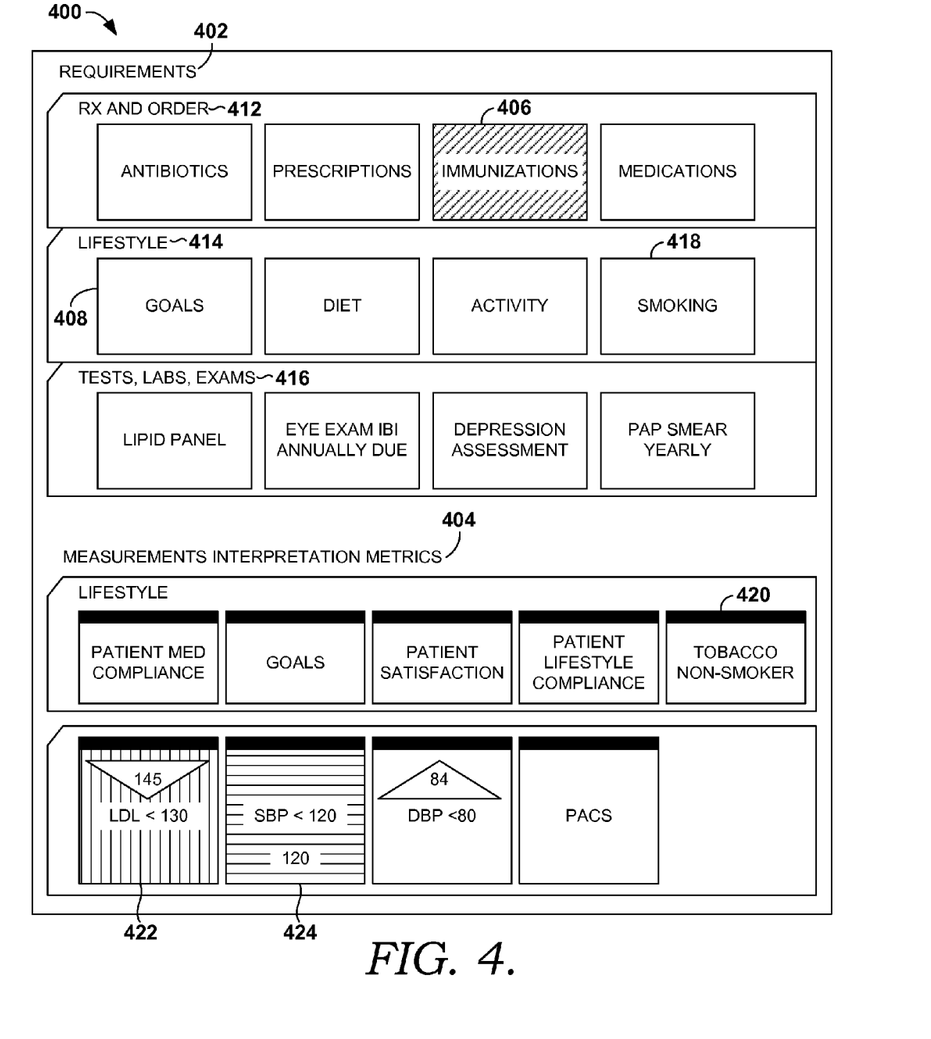
FIGS. 4-6 depict exemplary graphical user interfaces of provider care cards in accordance with embodiments of the present invention.

Turning now to FIG. 4, an exemplary graphical user interface (GUI) 400 of a provider care card is shown. As mentioned above, provider care cards are built upon relevant healthcare data generated by the health information transformation system. These easy-to-use, flexible, adaptive care cards allow providers to more effectively care for their patients by providing them with a comprehensive view of their patient's health. In one aspect of the invention, GUI 400 comprises a requirements display area 402 configured to display at least one or more clinical measures 418 relating to at least one patient, and a measurements display area 404 configured to display at least one or more measurements 420 completed for one or more clinical measures 418 relating to at least one patient. As well, GUI 400 comprises a first plurality of microdisplays 406 configured to display a first visual indicator for each of the clinical measures that have been met, and a second plurality of microdisplays 408 configured to display a second visual indicator for each of the clinical measures that have not been met. For example, immunization 406 has been met and not smoking 418 has not been met. Clinical measures 418 may comprise any health-related concept that is used by a provider in the care of a patient. Examples include prescriptions, lifestyle, diet, activity, diseases, conditions, mental health, over-the-counter medications, homeopathic medications, herbal remedies, allergies, family support, age, and many more. Clinical measure 418 is considered met if the patient or provider has acted with respect to clinical measure 418. For example, a clinical measure relating to a lipid panel would be met if the patient or provider drew a sample of the patient's blood and obtained a lipid panel.

In one aspect of the invention, requirements display area 402 may comprise at least an Order and Prescription area 412, a Lifestyle area 414, and a Tests, Labs, and Exams area 416. Order and Prescription area 412 may have an antibiotics area that contains information, for example, on which antibiotics a patient is taking, or which antibiotics a patient is allergic to, a prescription area containing information, for example, on which prescriptions the patient is currently taking, a medication area that documents all over-the-counter medications the patient is taking, and an immunization area that may contain information on the current immunization status of the patient.

Lifestyle area 414 may comprise a goals area containing information on provider goals for a patient. Provider goals may include general goals, specific goals, long-range goals, or short-range goals for patient care. By way of illustrative example, a provider may have a bed-ridden patient suffering from obesity, high blood pressure, and pressure sores. The provider's goals for this patient may include general, long-range goals such as having the patient lose weight and begin walking within the next three months, and specific, short-term goals such as having a home health nurse visit the patient and provide wound care for the pressure sores within the next week. Lifestyle area 414 may also comprise a diet area relating to dietary goals and restrictions for the patient, an activity area containing information on, for example, current activity and desired activity, and a smoking area containing information about the patient's tobacco history. Still further, Tests, Labs, and Exams area 416 may comprise such information as a lipid panel, depression assessment, blood pressure screening, eye exam, foot exam, pap smear, blood metabolic panel, thyroid panel, and the like.

In another aspect of the invention, requirements display area 402 may be customized to at least one or more conditions of the patient. A condition may be defined as the presence of illness, disease, or a state not normally present in the patient such as pregnancy. By way of illustrative example, and not by limitation, a patient suffering from cancer may have a cancer area within the requirements display area 402. The cancer area may contain clinical measures 418 specific to that condition such as a clinical measure 418 on how much radiation the patient has received in the course of her cancer treatment, or a clinical measure 418 concerning clinical studies in which the patient is enrolled.

As mentioned above, measurements display area 404 is configured to display one or more measurements 420 completed for one or more clinical measures 418 relating to a patient. Measurements 420 may comprise patient compliance, cost of care, patient satisfaction, patient lifestyle compliance, patient goal compliance, results of blood work or procedures, blood pressure readings, potentially avoidable complications (PAC), and the like. PACs may be defined as non-typical services associated with the care of a patient with a chronic condition. For example, diabetic patients typically have circulatory problems and neurological problems especially with respect to their feet. A typical service for a patient that is being followed for diabetes is a regular foot exam. A PAC associated with diabetes would be wound care for a diabetic patient with a foot ulcer who was not receiving regular foot exams.

In one aspect of the invention, measurement display area 404 may be configured to display measurements trends for at least one or more of measurements 420. Measurement trends for measurements 420 may be shown, for example, by an arrow, graph, table, chart, and such. This is useful, for example, when a provider is following the blood glucose levels of a diabetic patient. As well, measurement display area 404 may be configured to receive at least one or more measurements 420 from the patient. Measurements 420 may be electronically sent by the patient, received via a telephone call from the patient and inputted by the provider or someone from her staff, and the like.

Measurement display area 404 may also be configured to display comparisons between at least one or more measurements 420 of the patient and measurements 420 of a comparison group. The comparison may be at least one of condition-based, outcome-based, demographic-based, financial-based, geographic-based, and such. By way of illustrative example, a provider may be interested in comparing the cost of care for Patient X who has diabetes. The provider could access a condition-based and financial-based comparison of patient X and a comparison group. The comparison group could comprise other diabetic patients seen by the provider, diabetics within a certain zip code, diabetic patients from the population at large, and so on. The use of comparisons gives the provider important feedback regarding the quality of care the provider is delivering to her patient.

Continuing on, measurement display area 404 may be configured to display a third visual indicator 422 if measurement 420 is abnormal and a fourth visual indicator 424 if measurement 420 is normal. For example, third visual indicator 422 indicates that the patient has an abnormal LDL, and fourth visual indicator 424 indicates that the patient's systolic blood pressure is normal. By way of illustrative example, and not by limitation, third visual indicator 422 may be colored red to alert the provider that measurement 420 is abnormal. Additionally, fourth visual indicator 424 may be colored green to alert the provider that measurement 420 is within normal range. In one aspect of the invention, an alert, notification, or questionnaire may be automatically sent to the patient if measurement 420 is abnormal as shown by third visual indicator 422. The alert, notification or questionnaire may be sent via email, text message, automated phone call, and such. By way of illustrative example, and not by limitation, a diabetic patient may be responsible for monitoring his blood glucose levels at home and sending them to the provider. If the blood glucose levels are outside the normal range, a questionnaire may be automatically sent to the patient through electronic mail asking the patient what his symptoms are and requesting that a repeat blood glucose level be drawn and the results sent to the provider.

In one aspect of GUI 400, first plurality of microdisplays 406 are shaded a first color to indicate clinical measure 418 has been met, and second plurality of microdisplays 408 are shaded a second color to indicate clinical measure 418 has not been met. But it should be understood that any number of visual indicators may be used to indicate whether the clinical measure has been met/not met including words, symbols, patterns, and the like.

Additionally, at least one of second plurality of microdisplays 408 may be actionable meaning that a provider can click on the microdisplay 408 and initiate at least one of an ordering conversation, a quality measure conversation, a data review conversation, a document conversation, a scheduling conversation, a billing conversation, or a communication conversation. Upon clicking at least one of second plurality of microdisplays 408, the provider may be taken to computer interface that allows the provider, for example, to retrieve or view a document associated with the patient, order a test, procedure, or service for the patient, schedule the patient for a visit with the provider, retrieve quality measures, or initiate a communication with the patient through the use of, for example, electronic mail, text messaging, and the like. Using the example set out above concerning the patient suffering from obesity, hypertension, and pressure sores, an order conversation may comprise the provider ordering a home health nurse to visit the patient since the patient is bed-ridden in his home, while a document conversation may comprise the provider retrieving a consult letter from a bariatric physician who recently saw the patient. In addition, a communication conversation may comprise the provider sending an electronic message to the patient inquiring as to the status of the patient's pressure sores.

In another aspect of the invention, first plurality of microdisplays 406 may have mouse hover capabilities allowing the provider to hover over at least one of first plurality of microdisplays 406 and view information concerning that microdisplay. Such information may comprise lab results, examination results, procedure results, evaluation reports, and the like. Additionally, first plurality of microdisplays 406 and second plurality of microdisplays 408 may be organized into patient responsible tasks and provider responsible tasks. By way of illustrative example, and not by limitation, a patient responsible task may be to monitor blood pressure readings at home. The patient would be responsible for taking the blood pressure reading and communicating this reading to the provider through electronic mail, text messaging, a telephone call, and the like. Likewise, a provider responsible task in the above example, may comprise ordering a prescription for antihypertensive medication if the blood pressure readings are above a certain level. The provider could accomplish this task, for example, by initiating an ordering conversation through second plurality of microdisplays 408.

Figure 5:
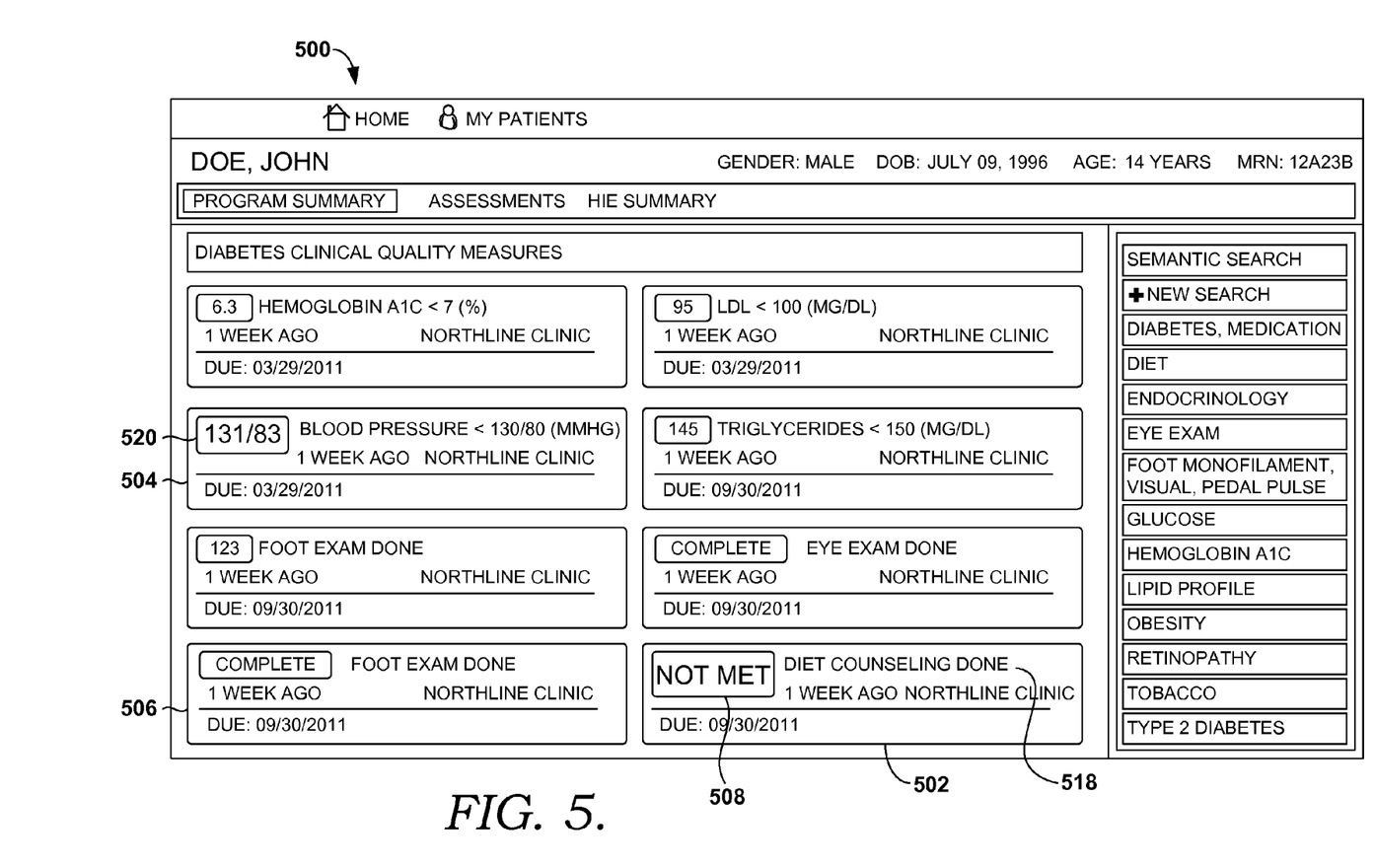

FIG. 5 represents another exemplary graphical user interface (GUI) 500 of a provider care card in accordance with an aspect of the present invention. GUI 500 comprises a requirements display area 502 configured to display at least one or more clinical measures 518 relating to at least one patient. Requirements display area 502 corresponds, for example, to requirements display area 402 of FIG. 4. As well, GUI 500 comprises a measurements display area 504 configured to display one or more measurements 520 completed for one or more clinical measures 518 relating to at least one patient. Continuing, GUI 500 has a first plurality of microdisplays 506 configured to display a first visual indicator for each of the clinical measures 518 that have been met. First plurality of microdisplays 506 correspond generally, for example, to first plurality of microdisplays 406 of FIG. 4. Finally, GUI 500 comprises a second plurality of microdisplays 508 configured to display a second visual indicator for each of the clinical measures 518 that have not been met. Second plurality of microdisplays 508 corresponds, for example, to second plurality of microdisplays 408 of FIG. 4.

Figure 6:
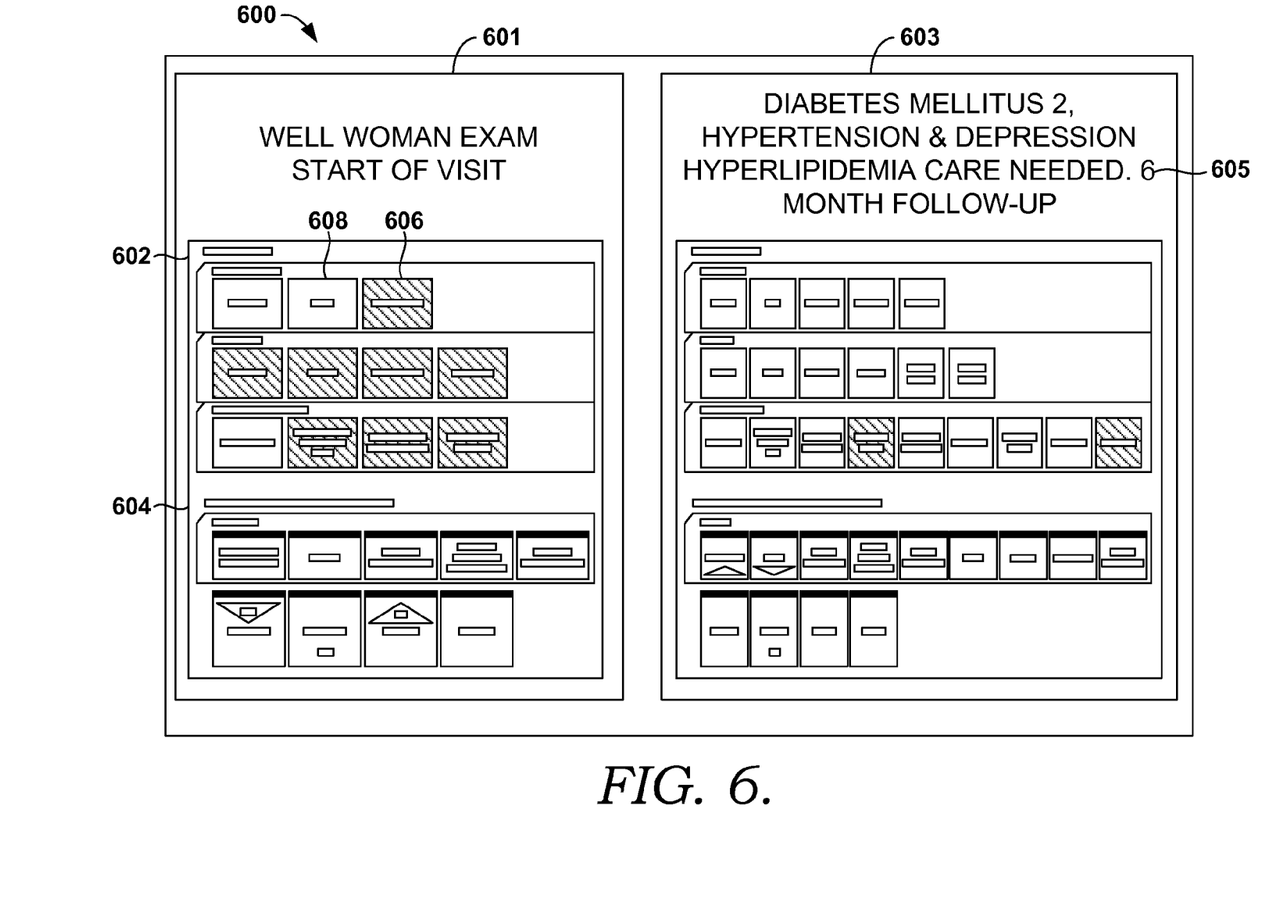

Turning now to FIG. 6, another exemplary graphical user interface 600 of a physician care card in accordance with an aspect of the present invention is shown. In one aspect, GUI 600 is configured to display at least one or more conditions 605 of the patient allowing a provider a comprehensive view of her patient's health. In yet another aspect of the invention, GUI 600 may be configured to allow the provider to select one or more condition-centric views for the patient. For example, a provider may have a patient with multiple conditions, but the provider wishes to focus on the condition that is the reason for the patient's present office visit to the provider. The provider may limit the display of GUI 600 to the condition at issue.

In addition, GUI 600 is configured to display a first plurality of microdisplays 606 and a second set of microdisplays 608 corresponding to first plurality of microdisplays 406 and second plurality of microdisplays 408 of FIG. 4. First plurality of microdisplays 606 and second plurality of microdisplays 608 may be arranged over a time period ranging from at least an initial point of provider/patient contact 601 to at least a current point of provider/patient contact 603 regardless of whether a clinical measure has been met. This view allows the provider to see how well he or she is doing in meeting clinical measures relating to the patient. For example, the provider would likely be delivering quality healthcare if the majority of visual indicators indicate that clinical measures have been met for the patient. Alternatively, if the majority of visual indicators indicate that the clinical measures have not been met for the patient, the provider could use this information to improve her practice. In addition, if there are patient responsible tasks, the provider would be able to see how well the patient is doing in taking responsibility for her own health care by checking to see if the visual indicators associated with the patient responsible tasks indicate that the clinical measures have been met.

Patient Care Cards

Figure 7:
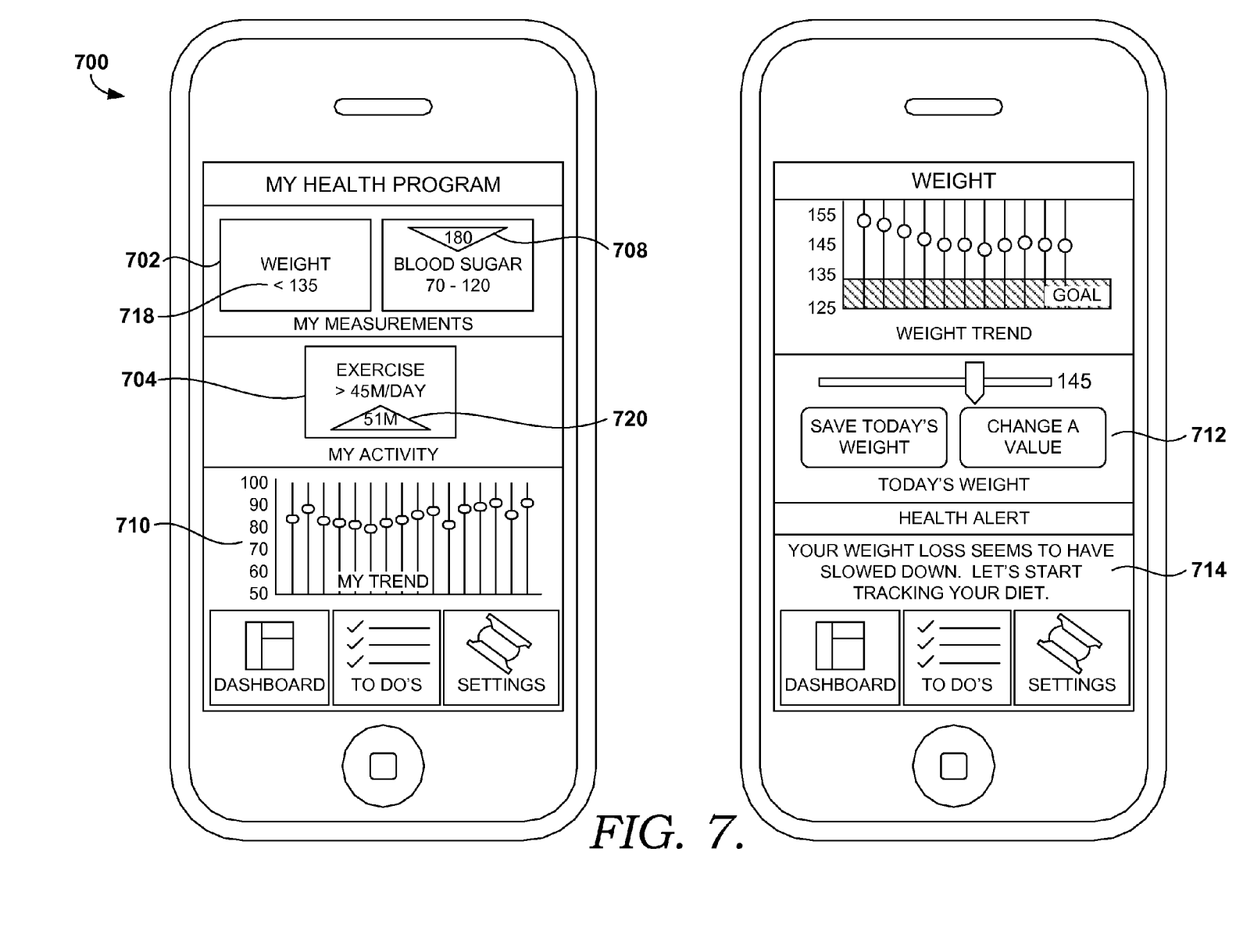
FIG. 7 depicts an exemplary graphical user interface of a patient care card in accordance with an embodiment of the present invention.

Turning now to FIG. 7, an exemplary graphical user interface (GUI) 700 of a patient care card in accordance with an embodiment of the present invention is provided. As mentioned above, patient care cards are built upon the relevant healthcare data that is generated through the health information transformation system. The patient care card is a user-friendly GUI that helps patients assume a more active role in managing their health.

In one aspect, GUI 700 comprises a requirements display area 702 that is configured to display at least one or more clinical measures 718 relating to a patient. Also, GUI 700 comprises a visual indicator 708 that changes depending on whether the at least one or more clinical measures 718 has been met or not met. Clinical measures 718 may comprise any healthcare-related concept that is used in patient care. Clinical measure 718 is met if a patient has acted with respect to clinical measure 718. For example, clinical measure 718 for a diabetic patient may include blood glucose levels. Clinical measure 718 is met if the patient takes a blood glucose reading and inputs it into GUI 700. Additionally, visual indicator 708 comprises any number of indicators such as, for example, color-coding, symbols, words, shading, and such. In one aspect, visual indicator 708 may be shaded a first color to indicate clinical measure 718 has been met, or visual indicator 708 may be shaded a second color to indicate that clinical measure 718 has not been met.

GUI 700 may be configured to display at least one or more conditions of the patient. And, further, the displayed clinical measures 718 may be customized to the at least one or more conditions of the patient. Thus, for example, a patient care card for a patient suffering from depression and diabetes may display clinical measures 718 related to both of these conditions such as blood glucose levels, a depression symptom checklist, and an exercise log.

In another aspect, GUI 700 comprises a requirements display area 702 configured to display at least one or more clinical measures 718 relating to a patient, a measurements display area 704 configured to display one or more measurements 720 completed for one or more clinical measures 718 relating to the patient, a visual indicator 708 that changes depending on whether the at least one or more clinical measures 718 has been met, and a trend display area 710 configured to display at least one or more graphical representations of clinical measures 718 relating to the patient. Measurements 720 may comprise results of blood work or procedures, blood pressure readings, blood glucose levels, exercise logs, completed symptom checklists, weight readings, and the like. In turn, graphical representations associated with trend display area 710 may include bar graphs, scatter plots, pie charts, pictographs, line graphs, histograms, and the like.

In one aspect, measurement display area 704 may be configured to display a first indicator if measurement 720 is abnormal, and a second indicator if measurement 720 is within normal limits. First and second indicators may include visual indicators such as color, shading, and words, and auditory indicators such as alarms, chimes, rings, and such. If measurement 720 is abnormal, a health alert display area 714 may be configured to display a message. In one aspect, the message may be sent by the patient's provider in response to the receipt of abnormal measurement 720. In another aspect, the message may be automatically generated upon detection of abnormal measurement 720.

In another aspect, measurements display area 704 may be configured to display comparisons between measurement 720 of the patient and measurement 720 of a comparison group. The comparison may be at least one of condition-based, demographic-based, cost-based, or geographic-based. The use of comparisons allows the patient, for example, to determine if the care she is receiving from her provider is not only cost-efficient, but also effective.

Continuing on, GUI 700 may be configured to be actionable. In one aspect, the action comprises a communication conversation with a provider, or a scheduling conversation with a provider. For example, Patient X may be concerned with measurement 720. Patient X is able to click on measurement 720 to access a communication screen. Patient X then inputs his message, and the message is electronically sent to the patient's provider. Or Patient X may wish to schedule an appointment with his provider; Patient X may access a scheduling screen and schedule the appointment. As well, GUI 700 may be configured to have hover capabilities allowing the patient to hover over one or more clinical measures 718 or measurements 720 and view healthcare information related to the one or more clinical measures 718 or measurements 720. By way of illustrative example, and not by limitation, Patient X would like to have more information about clinical measure 718 relating to weight. Patient X could hover over clinical measure 718 dealing with weight and access informational material on weight.

In another aspect, GUI 700 is configured to receive documentation, scheduling information, messages, measurements, or orders relating to at least one or more clinical measures 718 from at least one or more providers. Thus, if a patient recently had blood drawn at her provider's office, the provider could electronically send the results to the patient obviating the need for a phone call. If the blood work is abnormal, a message may be sent along with the results and displayed in health alert display area 714. The message would alert the patient and request that she contact the provider. In one aspect, a provider may send a post-treatment survey to the patient. The feedback provided by the survey furthers the goal of improving the quality of healthcare delivered by the provider.

In yet another aspect, GUI 700 comprises a requirements display area 702 configured to display at least one or more clinical measures 718 relating to a patient, and a measurements display area 704 configured to display one or more measurements 720 relating to the patient. As well, GUI 700 comprises a first visual indicator 708 that changes depending on whether the at least one or more clinical measures 718 has been met, a trend display area 710 configured to display at least one or more graphical representations of the clinical measures 718 relating to the patient, and a patient input display area 712 configured to receive inputs from the patient, where the inputs correspond to at least one or more of clinical measures 718 relating to the patient. Patient input display area 712 may be configured to receive inputs from the patient regarding whether to save measurement 720, change a value associated with clinical measure 718 (such as setting a new weight goal), or delete measurement 720 or clinical measure 718.

GUI 700 may also be configured to display a control panel, where the control panel comprises at least one of a to-do list, a settings panel, or a dashboard panel. The dashboard panel may be configured to allow the patient access to a variety of suitable healthcare-related applications.

Conclusion

As can be seen, embodiments of the present invention provide systems, methods, and computer-readable media for, among other things, transforming raw healthcare data into relevant data through the use of natural language processing, nomenclature and ontology mapping, and distributed adaptive knowledge processing. This relevant data, in turn, may be used to create decision support for use by, among other things, provider and patient care card applications. These care cards have a number of different capabilities that allow providers to more effectively care for their patients, and allow patients to more effectively partner with their providers in managing their health.

While the invention is susceptible to various modifications and alternative constructions, certain illustrated embodiments thereof are shown in the drawings and have been described above in detail. It should be understood, however, that there is no intention to limit the invention to the specific forms disclosed, but on the contrary, the intention is to cover all modifications, alternative constructions, and equivalents falling within the spirit and scope of the invention.

The present invention has been described in relation to particular embodiments, which are intended in all respects to be illustrative rather than restrictive. Alternative embodiments will become apparent to those of ordinary skill in the art to which the present invention pertains without departing from its scope.

The invention claimed is:

1. One or more non-transitory computer storage media having computer-useable instructions embodied thereon that, when executed by a computing device, cause the computing device to display a graphical user interface for presenting to a provider clinical measures and measurements related to a single patient, the graphical user interface comprising:
   a requirements display area configured to display only one or more selectable microdisplays relating solely to the single patient, each selectable microdisplay of the one or more selectable microdisplays displaying a clinical measure relating to the single patient, the clinical measure comprising a health-related concept used by the provider in the care of the single patient, wherein selection of at least one of the one or more selectable microdisplays initiates at least one of an order conversation, a document conversation, a scheduling conversation, or a communication conversation, and wherein:
   (1) at least a first portion of the one or more selectable microdisplays is shaded a first color indicating that the clinical measures represented by the at least the first portion of the one or more selectable microdisplays have been acted upon by at least one of the provider or the patient, the at least the first portion of the one or more selectable microdisplays shaded the first color comprising a first plurality of microdisplays,
   (2) at least a second portion of the one or more selectable microdisplays is shaded a second color indicating that the clinical measures represented by the at least the second portion of the one or more selectable microdisplays have not been acted upon by the at least one of the provider or the patient, the at least the second portion of the one or more selectable microdisplays shaded the second color comprising a second plurality of microdisplays, (3) the one or more selectable microdisplays are categorized into a prescription and order section, a lifestyle section, and a tests, labs and exam section based on the microdisplay's respective clinical measure, and wherein in each section, the section's corresponding selectable microdisplays are arranged in a patient-responsible group and a provider-responsible group, and wherein within each group the selectable microdisplays are arranged in a chronological order from at least an initial point of provider/patient contact to at least a current point of provider/patient contact; and a measurements display area configured to only display one or more measurements completed for the single patient.

2. The one or more non-transitory computer storage media of claim 1, wherein the graphical user interface is configured to allow a provider to select one or more condition-centric views.

3. The one or more non-transitory computer storage media of claim 2, wherein the displayed clinical measures are customized based on the selected one or more condition-centric views to the at least one or more conditions of the patient.

4. The one or more non-transitory computer storage media of claim 1, wherein the communication conversation occurs between the provider and the patient.

5. The one or more non-transitory computer storage media of claim 1, wherein the prescription and order section order and prescription area comprises at least one of prescriptions, immunizations, antibiotics, or medications.

6. The one or more non-transitory computer storage media of claim 1, wherein the lifestyle section comprises at least one of goals, diet, activity, or smoking.

7. The one or more non-transitory computer storage media of claim 1, wherein the measurements display area is configured to display comparisons between the one or more measurements completed for the single patient and measurements of a comparison group.

8. The one or more non-transitory computer storage media of claim 7, wherein the comparison is at least one of condition-based, demographic-based, cost-based, or geographic-based.

9. The one or more non-transitory computer storage media of claim 1, wherein the measurements display area is further configured to display measurement trends for the one or more measurements completed for the single patient.

10. The one or more non-transitory computer storage media of claim 1, wherein the measurements display area is further configured to display a first visual indicator if a measurement of the one or more measurements completed is abnormal, and further wherein the measurements display area is configured to display a second visual indicator if a measurement of the one or more measurements completed is normal.

11. The one or more non-transitory computer storage media of claim 10, wherein a questionnaire is electronically sent to the patient if the measurement of the one or more measurements completed is abnormal.

12. The one or more non-transitory computer storage media of claim 1, wherein the measurements display area is further configured to display potentially avoidable complications for the single patient.

13. The one or more non-transitory computer storage media of claim 1, wherein at least one of the one or more of the first plurality of selectable microdisplays is configured to have mouse hover capabilities.

* * * * *